(12) United States Patent
Chang et al.

(10) Patent No.: US 11,304,839 B2
(45) Date of Patent: Apr. 19, 2022

(54) LIFTING BELT

(71) Applicants: Ki Yong Chang, Seoul (KR); Min Young Kang, Seoul (KR)

(72) Inventors: Ki Yong Chang, Seoul (KR); Min Young Kang, Seoul (KR)

( * ) Notice: Subject to any disclaimer, the term of this patent is extended or adjusted under 35 U.S.C. 154(b) by 872 days.

(21) Appl. No.: 15/776,079

(22) PCT Filed: Mar. 10, 2017

(86) PCT No.: PCT/KR2017/002630
§ 371 (c)(1),
(2) Date: May 15, 2018

(87) PCT Pub. No.: WO2018/143508
PCT Pub. Date: Aug. 9, 2018

(65) Prior Publication Data
US 2020/0281752 A1 Sep. 10, 2020

(30) Foreign Application Priority Data
Feb. 1, 2017 (KR) .......................... 10-2017-0014561

(51) Int. Cl.
| | | |
|---|---|---|
| A61F 5/02 | (2006.01) | |
| A61F 5/042 | (2006.01) | |
| A61H 11/00 | (2006.01) | |
| A61H 1/02 | (2006.01) | |
| A61F 5/32 | (2006.01) | |

(52) U.S. Cl.
CPC .............. *A61F 5/028* (2013.01); *A61F 5/024* (2013.01)

(58) Field of Classification Search
CPC ................ A61F 5/02–048; A61F 5/058; A61F 5/05816; A61F 5/30–34; A61F 13/14–145; A61F 13/148; A61H 11/00; A61H 2011/005; A61H 2201/0103; A61H 2201/0192; A61H 2201/1619; A61H 2201/1621; A61H 2201/165;
(Continued)

(56) References Cited

U.S. PATENT DOCUMENTS 4,135,503 A * 1/1979 Romano ................. A61F 5/028
128/118.1
4,178,922 A * 12/1979 Curlee ...................... A61F 5/34
602/19
(Continued)

FOREIGN PATENT DOCUMENTS

| AU | 8175191 | 2/1992 |
|---|---|---|
| CN | 102579175 | 7/2012 |

(Continued)

OTHER PUBLICATIONS

"International Search Report (Form PCT/ISA/210)" of PCT/KR2017/002630, dated Nov. 1, 2017, pp. 1-3.
(Continued)

*Primary Examiner* — Michelle J Lee
(74) *Attorney, Agent, or Firm* — JCIPRNET (57) ABSTRACT

A lifting belt includes a lifter configured to generate a tractive force in a longitudinal direction of a spinal column by expansion, a left connector and a right connector respectively disposed on a left side and a right side of the lifter, and a central connector attachable to or detachable from the left connector and the right connector.

9 Claims, 6 Drawing Sheets

(58) Field of Classification Search
CPC .............. A61H 2201/1652; A61H 1/02; A61H 1/0218; A61H 1/0229; A61H 1/0292
See application file for complete search history.

(56) References Cited

U.S. PATENT DOCUMENTS

| | | | |
|---|---|---|---|
| 4,836,194 A * | 6/1989 | Sebastian | A61F 5/028 128/DIG. 20 |
| 5,503,620 A | 4/1996 | Danzger | |
| 5,728,055 A * | 3/1998 | Sebastian | A61F 5/012 128/100.1 |
| 8,172,779 B2 * | 5/2012 | Ingimundarson | A61F 5/028 602/19 |
| 8,864,695 B2 * | 10/2014 | Thornton | A61F 5/028 602/19 |
| 2003/0149390 A1 | 8/2003 | Lee | |
| 2007/0073204 A1 | 3/2007 | Suarez et al. | |
| 2008/0234617 A1 * | 9/2008 | Lee | A61F 5/028 602/19 |
| 2010/0262056 A1 | 10/2010 | Lusky et al. | |
| 2016/0006467 A1 | 1/2016 | Bogdan | |
| 2016/0206467 A1 * | 7/2016 | Glace | A61F 5/028 |
| 2018/0338853 A1 * | 11/2018 | Chang | A61F 5/024 |

FOREIGN PATENT DOCUMENTS

| | | | | |
|---|---|---|---|---|
| CN | 103582467 | 2/2014 | | |
| CN | 104068954 | 10/2014 | | |
| CN | 104800045 | 7/2015 | | |
| CN | 105208885 | 12/2015 | | |
| EP | 2529709 | 12/2012 | | |
| FR | 2910270 | 6/2008 | | |
| GB | 121067 A | * | 12/1918 | ............... A61F 5/03 |
| GB | 2339140 | 1/2000 | | |
| KR | 200193763 | 8/2000 | | |
| KR | 20070018407 | 2/2007 | | |
| KR | 100997574 | 11/2010 | | |
| KR | 20120110814 | 10/2012 | | |
| KR | 20130095935 | 8/2013 | | |
| KR | 101563149 | 10/2015 | | |
| WO | 2013189831 | 12/2013 | | |

OTHER PUBLICATIONS

"Written Opinion of the International Searching Authority (Form PCT/ISA/237)" of PCT/KR2017/002630, dated Nov. 1, 2017, pp. 1-6.

* cited by examiner

LIFTING BELT

TECHNICAL FIELD

Example embodiments relate to a lifting belt, and more particularly, to a lifting belt of which a lifter is closely attached to a trunk between ribs and a pelvis to effectively generate a tractive force in a longitudinal direction of a spinal column.

BACKGROUND ART

A generally-used waist lifting belt may aid a disc in recovering from a deformed state to an original state by pulling a pelvis and a waist in opposite directions and lifting a space between vertebrae of a centrum in order not to receive a pressure of an upper body.

The generally-used waist lifting belt may mostly use an air injection method, which uses a tube including a plurality of air passages in a vertical direction in such a belt, and injects air into a shrunk tube and allows the tube to be expanded and stretched in a vertical direction in order to lift or support a waist.

However, such a generally-used waist lifting belt may press an abdomen and also intestines, and may thus induce indigestion, poor blood circulation, and the like, because a volume of the tube increases in inner and outer directions, in addition to the vertical direction, while the shrunk tube is being expanded by the injection of air.

In addition, since all the air passages are connected to one another, a disc may deteriorate when any one portion of the air passages is pressed and an air pressure is concentrated in another portion. Further, a portion that is lifted when a waist moves may be contracted again, and thus a lifting effect may not be generated at the time.

Thus, various types of a lifting belt are under development.

For example, Korean Patent Application No. 10-2012-0017357 filed on Feb. 21, 2012, discloses a waist lifting belt including an articulated joint.

DISCLOSURE OF INVENTION

Technical Problem

An aspect of the present disclosure provides a lifting belt of which a lifter is closely attached to a trunk between ribs and a pelvis to improve wearability and effectively generate a tractive force in a longitudinal direction of a spinal column.

Another aspect of the present disclosure also provides a lifting belt that may be easily and accurately arranged at a center of a trunk of a user.

Still another aspect of the present disclosure also provides a lifting belt of which a size is adjustable based on a body type or shape of a user to be maximally closely attached to a trunk of the user.

Yet another aspect of the present disclosure also provides a lifting belt of which a central connector does not overlap a lifter, or a left connector and a right connector do not overlap each other in the central connector.

Solution to Problem

According to an aspect of the present disclosure, there is provided a lifting belt including a lifter configured to generate a tractive force along a spinal column of a user in a longitudinal direction of the spinal column by expansion, a left connector and a right connector respectively disposed on a left side and a right side of the lifter, and a central connector attachable to or detachable from the left connector and the right connector.

The central connector may include an indicator configured to indicate a connection location of the left connector or the right connector based on a body size of the user.

A plurality of indicators may be provided as the indicator, and the indicators may be disposed separately from one another in a longitudinal direction of the central connector.

The indicator may include a curve indicating an edge of the left connector or an edge of the right connector, and lexical indicia indicating the body size of the user corresponding to the curve.

The left connector or the right connector may include a first fixing member of which an edge has a curvature corresponding to a curvature of the curve.

The first fixing member may be provided in a form of a circle, and the curve may be provided in a form of an arc which is a portion of the circle.

The central connector may further include a second fixing member attachable to or detachable from the first fixing member.

The first fixing member and the second fixing member may be provided as a hook-and-loop fastener. The first fixing member may be a hook portion of the hook-and-loop fastener, and the second fixing member may be a loop portion of the hook-and-loop fastener.

The left connector or the right connector may include an edging member extended from an upper end and a lower end of the lifter to cover an outer side of the left connector or the right connector. A sum of a distance from an end of the central connector to the indicator and a width of the edging member may be less than or equal to ½ of a total length of the central connector.

The lifter may include a plurality of expanding portions extended in the longitudinal direction of the spinal column and configured to be expanded by injection of a fluid, and a plurality of blocking portions disposed among the expanding portions in a vertical direction of the lifter.

The expanding portions may be disposed to a front side and a rear side from a side surface of a waist of the user.

A distance from an end of the left connector or the right connector to an expanding portion closest to the left connector or the right connector among the expanding portions may be greater than or equal to ½ of a total length of the central connector.

Each of the left connector and the right connector may include a first connecting member connected to the upper end of the lifter on a left side or a right side of the lifter, and a second connecting member connected to the lower end of the lifter on the left side or the right side of the lifter.

The central connector may include a first central connecting member to be connected to the first connecting member, and a second central connecting member to be connected to the second connecting member.

Advantageous Effects of Invention

According to example embodiments, a lifting belt may include a lifter closely attached to a trunk between ribs and a pelvis so that the lifting belt may become more wearable and more effectively generate a tractive force in a longitudinal direction of a spinal column.

According to example embodiments, a lifting belt may be easily and accurately arranged at a center of a trunk of a user.

According to example embodiments, a size of a lifting belt may be adjustable based on a body type or shape of a user, and thus a lifter of the lifting belt may be maximally closely attached to a trunk of the user.

According to example embodiments, a central connector of a lifting belt may not overlap a lifter, or a left connector and a right connector of the lifting belt may overlap each other in the central connector.

BEST MODE FOR CARRYING OUT THE INVENTION

Hereinafter, example embodiments will be described in detail with reference to the accompanying drawings. Regarding the reference numerals assigned to the elements in the drawings, it should be noted that the same elements will be designated by the same reference numerals, wherever possible, even though they are shown in different drawings. In the description of example embodiments, detailed description of well-known related structures or functions will be omitted when it is deemed that such description will cause ambiguous interpretation of the present disclosure.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected," "coupled," or "joined" to another component, a third component may be "connected," "coupled," and "joined" between the first and second components, although the first component may be directly connected, coupled or joined to the second component.

A component described in any one of the example embodiments and a component including a common function or feature will be described using the same names in other example embodiments. Unless otherwise stated, the description in any one of the example embodiments may be applicable to other example embodiments, and a detailed description will be omitted in an overlapping range.

Figure 1:
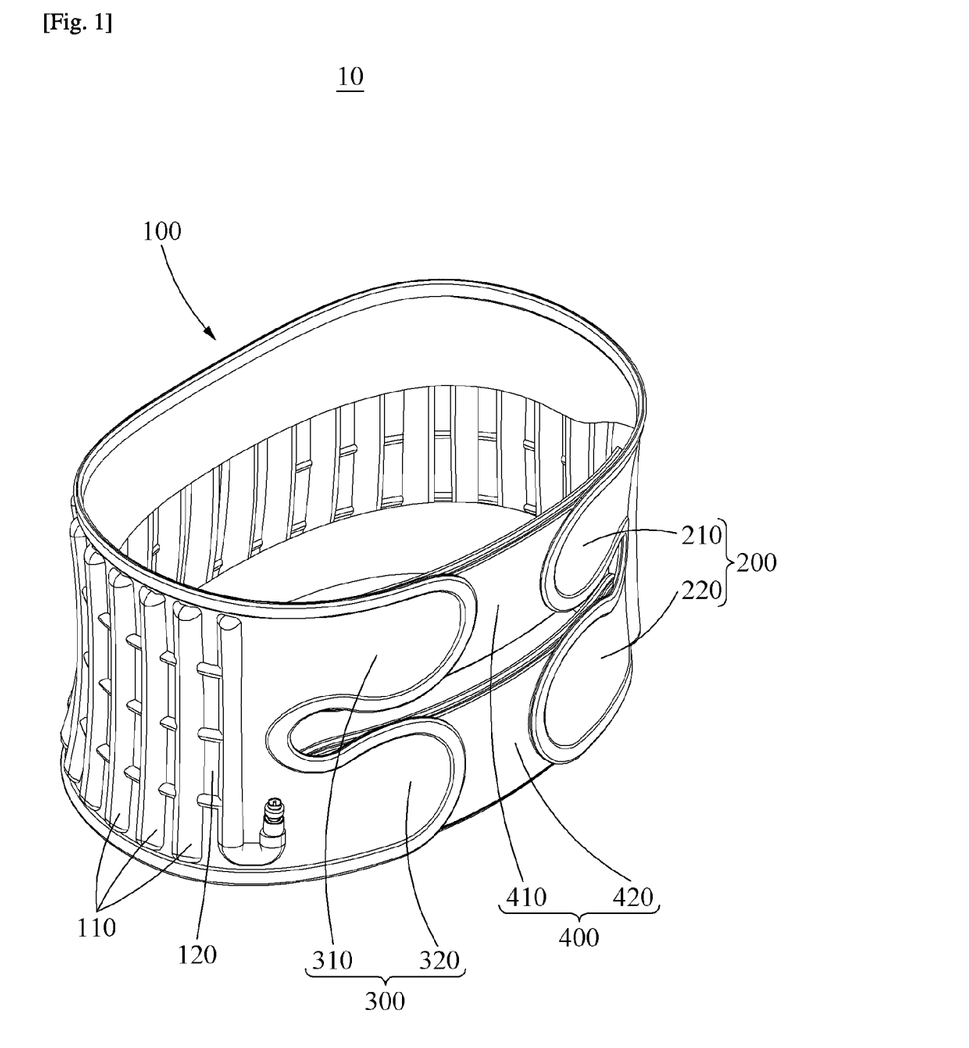
FIG. 1 is a perspective view of a lifting belt according to an example embodiment.
Figure 2A:
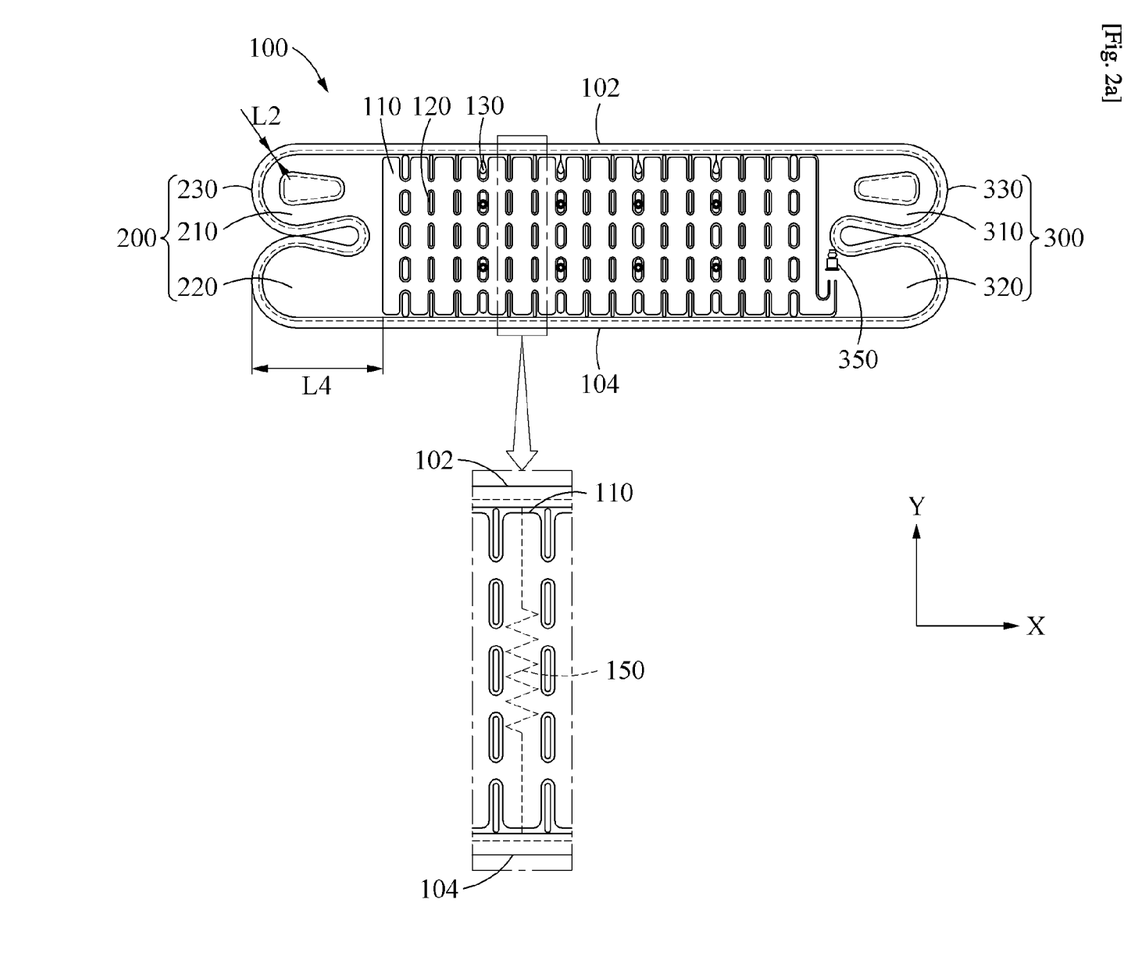
FIGS. 2a and 2b illustrate an outer side of a lifting belt according to an example embodiment.
Figure 2B:
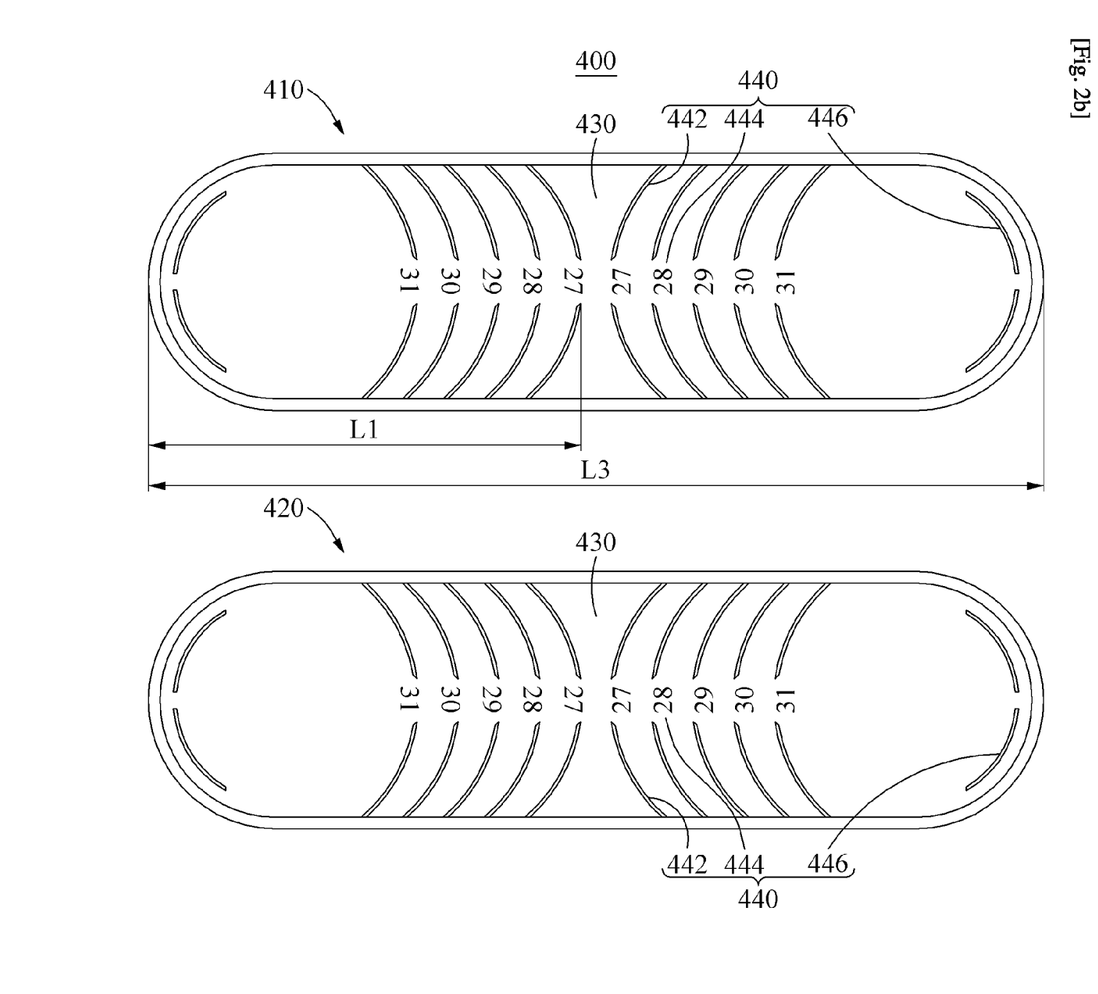
Figure 3A:
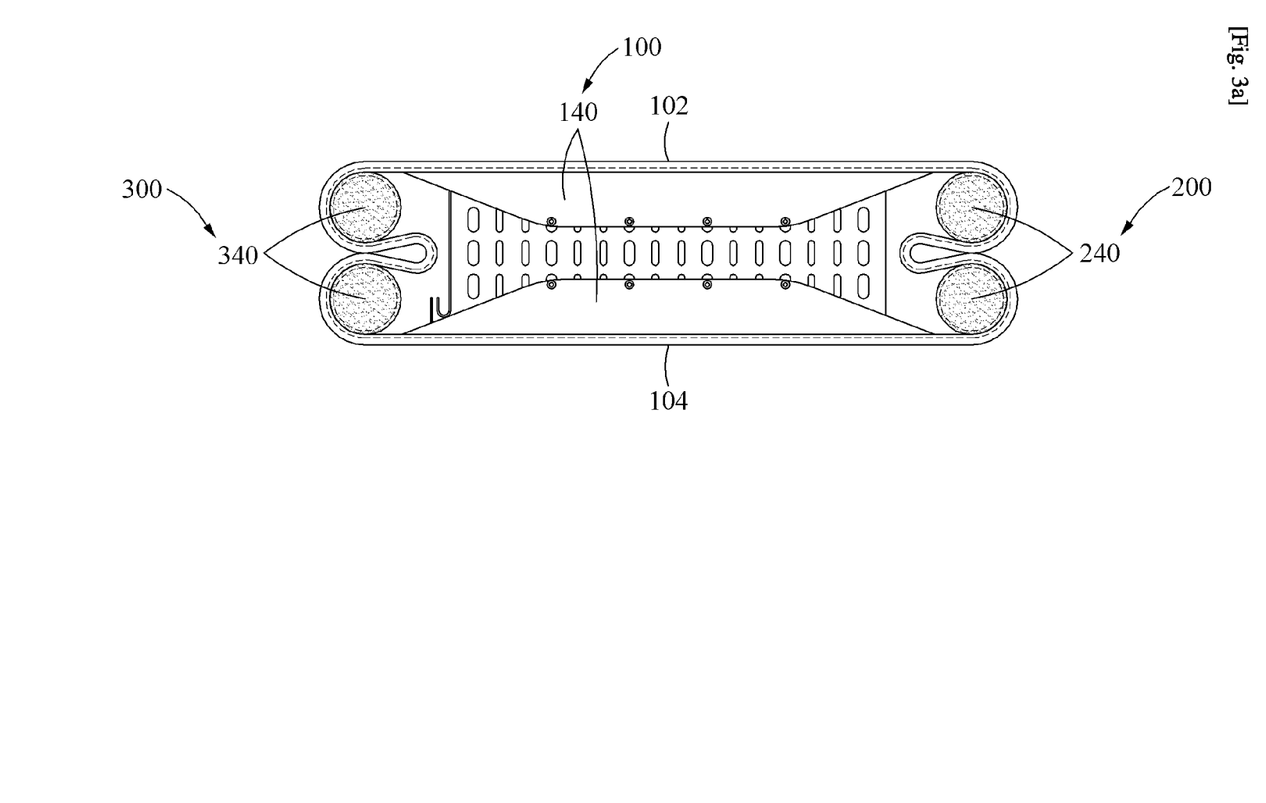
FIGS. 3a and 3b illustrate an inner side of a lifting belt according to an example embodiment.
Figure 3B:
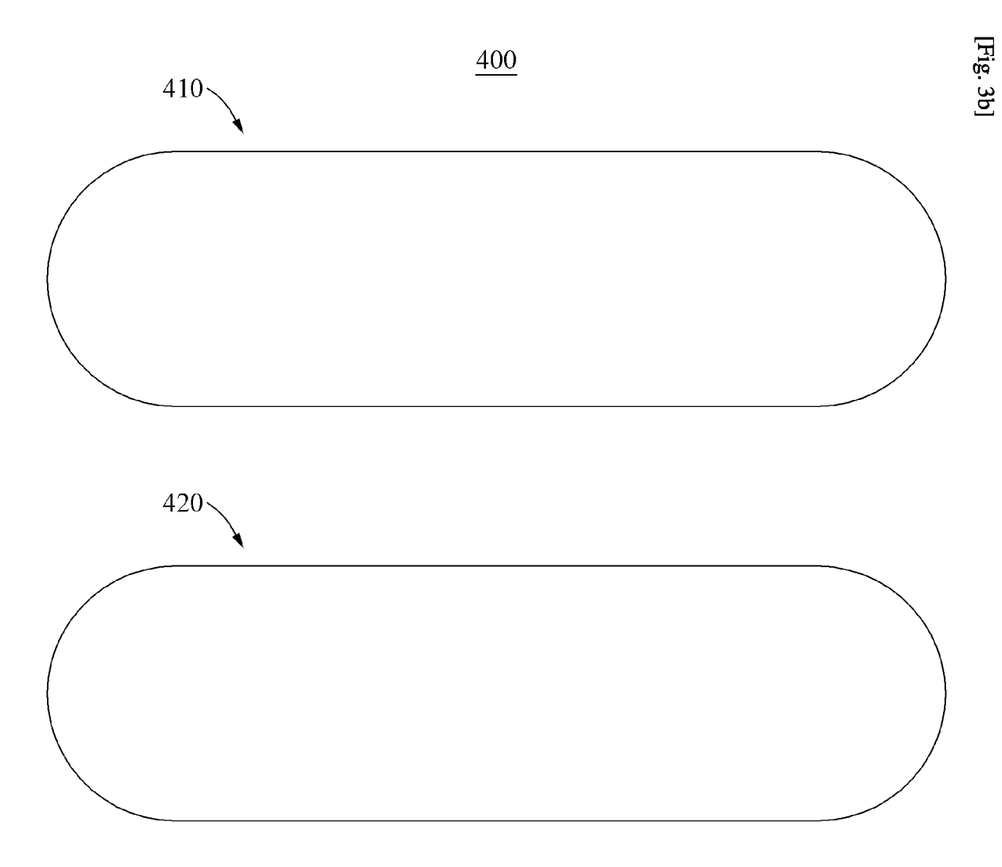
Figure 4:
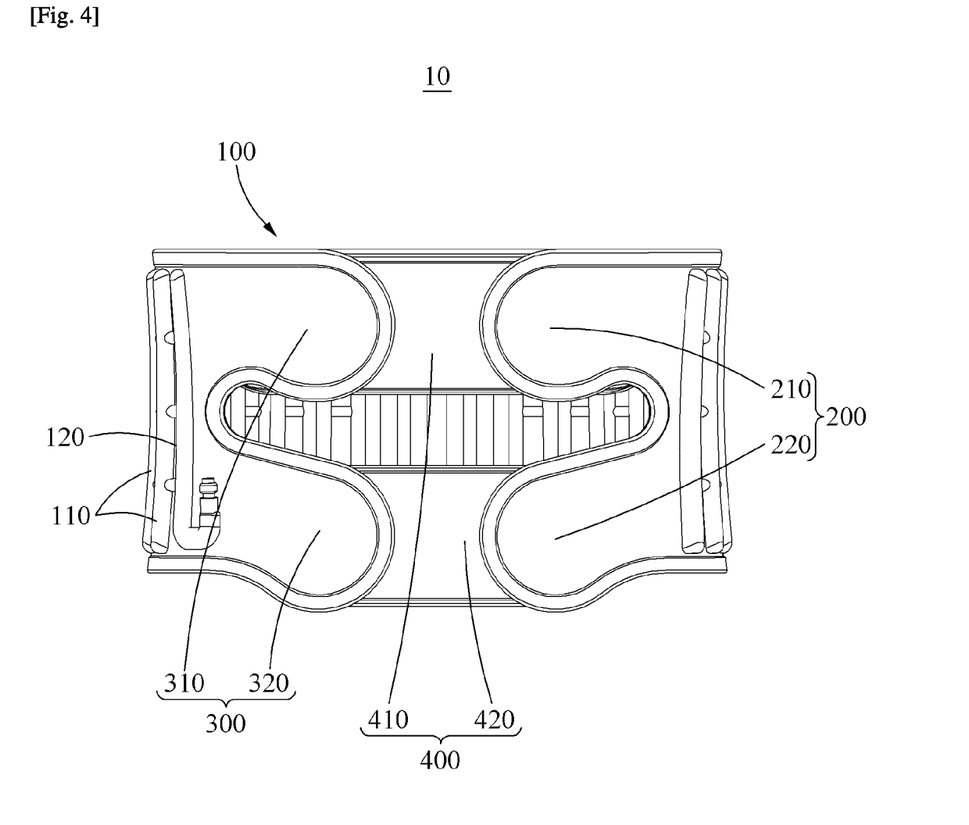
FIG. 4 illustrates a lifting belt worn around a trunk of a user according to an example embodiment.

FIG. 1 is a perspective view of a lifting belt according to an example embodiment. FIGS. 2a and 2b illustrate an outer side of a lifting belt according to an example embodiment. FIGS. 3a and 3b illustrate an inner side of a lifting belt according to an example embodiment. FIG. 4 illustrates a lifting belt worn around a trunk of a user according to an example embodiment.

Referring to FIG. 1, a lifting belt 10 includes a lifter 100, a left connector 200, a right connector 300, and a central connector 400.

The lifter 100 may generate a tractive force along a spinal column of a user in a longitudinal direction of the spinal column by expansion.

Referring to FIG. 2a, the lifter 100 has a length extended in a horizontal direction, or an X direction, along a trunk of the user, and also a length extended in a vertical direction, or a Y direction, along the spinal column in the longitudinal direction of the spinal column.

The lifter 100 includes a plurality of expanding portions 110, a plurality of blocking portions 120, and a plurality of cut portions 130.

The expanding portions 110 may be extended in the longitudinal direction of the spinal column, or in a vertical direction of the lifter 100. Thus, an end of the expending portions 110 may be disposed adjacent to an upper end 102 of the lifter 100, and another end of the expanding portions 110 may be disposed adjacent to a lower end 104 of the lifter 100.

In addition, the expanding portions 110 may be disposed separately from one another in a longitudinal direction of the lifter 100, or in a lateral direction or a horizontal direction of the lifter 100. Thus, some of the expanding portions 110 may be disposed adjacent to a left end of the lifter 100 or the left connector 200, and others of the expanding portions 110 may be disposed adjacent to a right end of the lifter 100 or the right connector 300.

The expanding portions 110 may be expanded by injection of a fluid, and such an expansion of the expanding portions 110 may enable the lifter 100 to generate the tractive force along the spinal column in the longitudinal direction of the spinal column.

Referring to FIG. 4, the expanding portions 110 may be disposed to a front side and a rear side from a side surface of a waist of the user. In detail, some of the expanding portions 110 may be disposed to the front side from the side surface of the waist, and remaining others of the expanding portions 110 may be disposed to the rear side from the side surface of the waist. Thus, when the expanding portions 110 are expanded, the tractive force may be generated to the side surface of the waist between a pelvis and ribs of the user.

The blocking portions 120 may be disposed in spaces between neighboring expanding portions among the expanding portions 110.

The blocking portions 120 may be extended in the longitudinal direction of the spinal column or in the vertical direction of the lifter 100, and disposed separately from one another in the vertical direction of the lifter 100.

A fluid may not be injected into the blocking portions 120, and only the expanding portions 110 may be expanded when the fluid is injected into the lifter 100.

Due to such a disposition of the expanding portions 110 and the blocking portions 120, a plurality of air columns extended upwards and downwards, or in a vertical direction, may be formed in the lifter 100.

In addition, through spaces between neighboring blocking portions among the blocking portions 120, a fluid may be transferred from one neighboring expanding portion to another neighboring expanding portion of the expanding portions 110.

As illustrated, a fluid injection member 350 may be disposed in the right connector 300 of the lifting belt 10, and thus a fluid injected into the fluid injection member 350 may have directivity from a right side to a left side.

The expanding portions 110 and the blocking portions 120 may be provided in the lifter 100 as described hereinafter.

For example, the blocking portions 120 may be provided by stacking two fabric layers of a same size and bonding the layers at a certain location using a high frequency, and the expanding portions 110 may be provided in spaces of the fabric layers that are not bonded by the high frequency.

However, a method of providing the expanding portions 110 and the blocking portions 120 in the lifter 100 is not limited to the example described in the foregoing, and thus any methods that may form an air column extended in the vertical direction of the lifter 100 may be applicable.

In addition, the cut portions 130 may be disposed adjacent to the upper end 102 of the lifter 100, among the expanding portions 110.

For example, the cut portions 130 may be extended towards the lower end 104 from the upper end 102 of the lifter 100. Here, a cut width of each of the cut portions 130 may increase towards the lower end 104 from the upper end 102 of the lifter 100.

The cut portions 130 may be disposed separately from one another in the lateral direction of the lifter 100, and three or four expanding portions of the expanding portions 110 may be disposed between the cut portions 130.

When a fluid is injected into the lifter 100, the expanding portions 110 may be expanded in the vertical direction of the lifter 100, and the cut width of the cut portions 130 may be decreased. Thus, a length of the upper end 102 of the lifter 100 may be shorter than a length of the lower end 104 of the lifter 100.

When the lifting belt 10 is worn on the user, the cut portions 130 may be used to prevent a compression by the lifter 100 from loosening in an upper portion of the waist of the user or an upper portion of an abdomen of the user.

Referring to FIG. 3a, the lifter 100 also includes at least one flap member 140.

The flap member 140 may be provided to cover an inner surface of the lifter 100.

For example, in a case that a plurality of flap members is provided as the flap member 140 to cover the inner surface of the lifter 100, one of the flap members may be extended to a center of the lifter 100 from the upper end 102 of the lifter 100, and another one of the flap members may be extended to the center of the lifter 100 from the lower end 104 of the lifter 100.

Alternatively, in a case that a single flap member is provided as the flap member 140 to cover the inner surface of the lifter 100, the single flap member may be extended towards the lower end 104 from the upper end 102 of the lifter 100, or extended towards the upper end 102 from the lower end 104 of the lifter 100.

Referring back to FIG. 2a, the lifter 100 further includes an elastic member 150 configured to connect an upper end and a lower end of the expanding portions 110 in the expanding portions 110.

The elastic member 150 may be stretchably deformed by expansion of the expanding portions 110, and the expanding portions 110 may return to an original state of the expanding portions 110 by contraction of the elastic member 150.

Referring back to FIG. 1, the left connector 200 and the right connector 300 may be connected to a left side and a right side of the lifter 100, respectively.

The left connector 200 may be disposed on a left side of the user and the right connector 300 may be disposed on a right side of the user, when the lifting belt 10 is worn on the user.

The left connector 200 and the right connector 300 may be symmetrical with each other relative to the lifter 100.

In detail, the left connector 200 includes a first left connecting member 210 that is connected to the upper end 102 of the lifter 100 on a left side of the lifter 100, and a second left connecting member 220 that is connected to the lower end 104 of the lifter 100 on the left side of the lifter 100. Similarly, the right connector 300 includes a first right connecting member 310 that is connected to the upper end 102 of the lifter 100 on a right side of the lifter 100, and a second right connecting member 320 that is connected to the lower end 104 of the lifter 100 on the right side of the lifter 100.

As described above, the lifting belt 10 may be provided as a double belt type of which the left connector 200 includes the first left connecting member 210 and the second left connecting member 220, and the right connector 300 includes the first right connecting member 310 and the second right connecting member 320, and thus may be maximally closely attached to the trunk of the user.

In general, a circumference of an upper portion of a waist of a user is smaller than a circumference of a lower portion of the waist due to a curve of the waist, and thus the upper end 102 of the lifter 100 may not be closely attached to the upper portion of the waist when a length of the upper end 102 of the lifter 100 is equal to a length of the lower end 104 of the lifter 100, and the tractive force generated by the lifter 100 may not be readily applied to the user.

Here, by adjusting a gap between the first left connecting member 210 and the first right connecting member 310, a total length of the upper end 102 of the lifter 100 may correspond to the circumference of the upper portion of the waist. Similarly, by adjusting a gap between the second left connecting member 220 and the second right connecting member 320, a total length of the lower end 104 of the lifter 100 may correspond to the circumference of the lower portion of the waist. Thus, the lifter 100 may be maximally closely attached to the waist, and the tractive force generated by the lifter 100 may be readily applied to the user.

Referring back to FIG. 2a, the left connector 200 and the right connector 300 further include a left edging member 230 and a right edging member 330, respectively, that are extended from the upper end 102 and the lower end 104 of the lifter 100 and provided to cover respective outer sides of the left connector 200 and the right connector 300.

In detail, the left edging member 230 may be extended from the upper end 102 and the lower end 104 of the lifter 100 to cover the outer side of the left connector 200, for example, respective outer sides of the first left connecting member 210 and the second left connecting member 220. Similarly, the right edging member 330 may be extended from the upper end 102 and the lower end 104 of the lifter 100 to cover the outer side of the right connector 300, for example, respective outer sides of the first right connecting member 310 and the second right connecting member 320.

Referring back to FIG. 3a, the left connector 200 or the right connector 300 includes a first fixing member.

The first fixing member may be a hook portion of a hook-and-loop fastener.

The first fixing member includes a first left fixing member 240 provided in the left connector 200 and a first right fixing member 340 provided in the right connector 300.

The first left fixing member 240 may be provided on an inner surface of the first left connecting member 210 and an inner surface of the second left connecting member 220. The first right fixing member 340 may be provided on an inner surface of the first right connecting member 310 and an inner surface of the second right connecting member 320.

The first left fixing member 240 and the first right fixing member 340 may be provided in a form of a circle. Here, a portion of the left edging member 230 provided in the left connector 200 may come in contact with an edge of the first left fixing member 240, and a curvature of an end portion of the left connector 200 may correspond to a curvature of the first left fixing member 240. Similarly, a portion of the right edging member 330 provided in the right connector 300 may come in contact with an edge of the first right fixing member 340, and a curvature of an end portion of the right connector 300 may correspond to a curvature of the first right fixing member 340.

Referring back to FIG. 1, the central connector 400 is provided to be attachable to or detachable from the left connector 200 and the right connector 300.

The central connector 400 includes a first central connecting member 410 and a second central connecting member 420.

The first central connecting member 410 may be disposed between the first left connecting member 210 and the first right connecting member 310, and the second central connecting member 420 may be disposed between the second left connecting member 220 and the second right connecting member 320.

Here, the first central connecting member 410 and the second central connecting member 420 may be provided in a same form, and extended along the trunk of the user in a lateral direction, or a left and right direction.

Referring to FIG. 2b, both ends of each of the first central connecting member 410 and the second central connecting member 420 may be provided in a curved form, and a curvature of the curved form may correspond to a curvature of the edge of each of the first left fixing member 240 and the first right fixing member 340.

The central connector 400 also includes a second fixing member 430 provided on an outer surface of the central connector 400, for example, the first central connecting member 410 and the second central connecting member 420.

The second fixing member 430 may be provided to be attachable to or detachable from the first left fixing member 240 and the first right fixing member 340.

For example, the second fixing member 430 may be provided as a loop portion of the hook-and-loop fastener, and an entire outer surface of the first central connecting member 410 and the second central connecting member 420 may be provided as the loop portion.

Referring to FIG. 3b, an inner surface of each of the first central connecting member 410 and the second central connecting member 420 may be provided as a smooth surface without uneven portions because the inner surface comes in contact with the trunk of the user.

As described above, the curvature of the both ends of each of the first central connecting member 410 and the second central connecting member 420 may correspond to the curvature of the edge of each of the first left fixing member 240 and the first right fixing member 340. In addition, the second fixing member 430 may be provided on the entire outer surface of the first central connecting member 410 and the second central connecting member 420. Thus, the first left fixing member 240 and the first right fixing member 340 may be attached to the second fixing member 430 so that the lifting belt 10 may be closely attached to the trunk of the user and arranged accurately at a center of the trunk of the user when adjusting a size of the lifting belt 10 to be suited to a body type or shape of the user.

Here, the first left fixing member 240 and the first right fixing member 340 may be provided in a form of a circle, and thus attaching and detaching the first left fixing member 240 and the first right fixing member 340 to and from the second fixing member 430 may be more readily performed.

Referring back to FIG. 2b, an indicator 440 is provided in the first central connecting member 410 and the second central connecting member 420 to indicate a connection location of the left connector 200 or the right connector 300 based on a body size of the user.

A plurality of indicators may be provided as the indicator 440, and the indicators may be disposed separately from one another in a longitudinal direction of the central connector 400.

Although the indicators are illustrated as being provided in both of the first central connecting member 410 and the second central connecting member 420, the indicator 440 may be provided in one of the first central connecting member 410 and the second central connecting member 420 or provided at one end of both ends of the first central connecting member 410 or one end of both ends of the second central connecting member 420.

In addition, the indicator 440 includes a first curve 442 indicating the edge of the left connector 200 or the edge of the right connector 300, and lexical indicia 444 indicating the body size of the user corresponding to the first curve 442.

For example, the first curve 442 may indicate a location at which the left edging member 230 of the left connector 200 or the right edging member 330 of the right connector 300 needs to be connected. The first curve 442 may be provided in a form of an arc, which is a portion of a circle.

Here, a curvature of the first curve 442 may correspond to the curvature of the both ends of the left connector 200 or the curvature of the both ends of the right connector 300. In addition, the curvature of the first curve 442 may correspond to the curvature of the first left fixing member 240 and the curvature of the first right fixing member 340.

The lexical indicia 444 may indicate a size of the waist of the user, for example, 27 inches, 28 inches, 29 inches, and 30 inches. However, examples of such an indication are not limited to the illustrative example, and thus the indication may be provided by the lexical indicator 444 by various forms, for example, characters and numerals.

The indicator 440 further includes a second curve 446.

The second curve 446 may indicate a location at which an edge of the first left fixing member 240 and the first right fixing member 340 that is close to the lifter 100 is to be connected. A curvature of the second curve 446 may correspond to the curvature of both ends of the first central connecting member 410 and the curvature of both ends of the second central connecting member 420.

As described above, the central connector 400 may be provided to be separable from the left connector 200 and the right connector 300, and the central connector 400 may include the indicator 440. Thus, the lifting belt 10 may be arranged accurately at the center.

In addition, referring to FIGS. 2a and 2b, a sum of a distance L1 from an end of the central connector 400 to the indicator 440 and a width L2 of an edging member 230 or 330 may be less than or equal to ½ of a total length L3 of the central connector 400.

In detail, a sum of a distance from the end of the central connector 400 to an indicator indicating a minimum size among the indicators provided as the indicator 440 and the width L2 of the edging member 230 or 330 may be equal to ½ of the total length L3 of the central connector 400. A sum of a distance from the end of the central connector 400 to an indicator indicating a relatively large size among the indicators provided as the indicator 440 and the width L2 of the edging member 230 or 330 may be less than ½ of the total length L3 of the central connector 400.

Thus, even when the lifting belt 10 is worn at the minimum size, an overlap between the left connector 200 and the right connector 300 may be prevented, and such a prevention may help improve wearability and close attachment.

In addition, a distance L4 from an end of the left connector 200 or the right connector 300 to an expanding portion closest to the left connector 200 or the right connector 300 among the expanding portions 110 may be greater than or equal to ½ of the total length L3 of the central connector 400.

Thus, even when the lifting belt 10 is worn at the minimum size, an overlap between the central connector 400 and the expanding portions 110 may be prevented, and such a prevention may help improve wearability and close attachment and also allow the tractive force generated by the lifter 100 to be transferred to the user effectively.

Referring back to FIG. 4, when the lifting belt 10 is worn around the trunk of the user, the first left connecting member 210 and the first right connecting member 310 may be attached to the first central connecting member 410 to be suited to the body type or shape of the user, and the second left connecting member 220 and the second right connecting member 320 may be attached to the second central connecting member 420 to be suited to the body type or shape of the user.

For example, a length externally exposed from the first central connecting member 410 may be shorter than a length externally exposed from the second central connecting member 420. In addition, by pulling the second left connecting member 220 and the second right connecting member 320 downwards and attaching the second left connecting member 220 and the second right connecting member 320 to the second central connecting member 420, after the first left connecting member 210 and the first right connecting member 310 are attached to the first central connecting member 410, the lifting belt 10 may be maximally closely attached to the side surface of the waist between the pelvis and the ribs of the user.

Here, the indicator 440 provided on the outer surface of the first central connecting member 410 and the second central connecting member 420 may facilitate a central arrangement. In addition, the second fixing member 430 provided on the outer surface of the first central connecting member 410 and the second central connecting member 420 may more readily attach or detach the left connector 200 and the right connector 300 to or from the central connector 400.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Therefore, the scope of the disclosure is defined not by the detailed description, but by the claims and their equivalents, and all variations within the scope of the claims and their equivalents are to be construed as being included in the disclosure.

The invention claimed is:

1. A lifting belt comprising:
a lifter configured to generate a tractive force in a longitudinal direction of a spinal column by expansion;
a left connector and a right connector respectively disposed on a left side and a right side of the lifter; and
a central connector attachable to or detachable from the left connector and the right connector,
wherein the left connector comprises:
a first connecting member connected to an upper end of the lifter on the left side of the lifter; and
a second connecting member connected to a lower end of the lifter on the left side of the lifter, and
the right connector comprises:
another first connecting member connected to an upper end of the lifter on the right side of the lifter, and
another second connecting member connected to a lower end of the lifter on the right side of the lifter,
wherein the central connector comprises:
a first central connecting member to be connected to the first connecting member and the another first connecting member; and
a second central connecting member to be connected to the second connecting member and the another second connecting member,
wherein the central connector comprises an indicator configured to indicate a connection location of the left connector or the right connector based on a body size of a user,
wherein the indicator comprises a curve indicating an edge of the left connector or an edge of the right connector, and lexical indicia configured to indicate the body size of the user corresponding to the curve.

2. The lifting belt of claim 1, wherein the left connector or the right connector comprises a first fixing member of which an edge has a curvature corresponding to a curvature of the curve.

3. The lifting belt of claim 2, wherein the central connector further comprises a second fixing member attachable to or detachable from the first fixing member.

4. The lifting belt of claim 3, wherein the first fixing member and the second fixing member are provided as a hook-and-loop fastener,
wherein the first fixing member is a hook portion of the hook-and-loop fastener, and
the second fixing member is a loop portion of the hook-and-loop fastener.

5. The lifting belt of claim 2, wherein the first fixing member is provided in a form of a circle, and
the curve is provided in a form of an arc which is a portion of the circle.

6. The lifting belt of claim 1, wherein a plurality of indicators is provided as the indicator,
wherein the plurality of indicators are disposed separately from one another in a longitudinal direction of the central connector.

7. A lifting belt comprising:
a lifter configured to generate a tractive force in a longitudinal direction of a spinal column by expansion;
a left connector and a right connector respectively disposed on a left side and a right side of the lifter; and
a central connector attachable to or detachable from the left connector and the right connector,
wherein the left connector comprises:
a first connecting member connected to an upper end of the lifter on the left side of the lifter; and
a second connecting member connected to a lower end of the lifter on the left side of the lifter, and
the right connector comprises:
another first connecting member connected to an upper end of the lifter on the right side of the lifter, and
another second connecting member connected to a lower end of the lifter on the right side of the lifter,
wherein the central connector comprises:
a first central connecting member to be connected to the first connecting member and the another first connecting member; and a second central connecting member to be connected to the second connecting member and the another second connecting member, wherein the lifter further comprises:

a plurality of expanding portions configured to extend in the longitudinal direction of the spinal column and configured to be expanded by injection of a fluid; and a plurality of blocking portions disposed among the plurality of expanding portions in a vertical direction of the lifter, wherein a distance from an end of the left connector or the right connector to an expanding portion closest to the left connector or the right connector among the plurality of expanding portions is greater than or equal to ½ of a total length of the central connector.

8. The lifting belt of claim 7, wherein the plurality of expanding portions are configured to be disposed to a front side and a rear side from a side surface of a waist.

9. A lifting belt comprising:

a lifter configured to generate a tractive force in a longitudinal direction of a spinal column by expansion;

a left connector and a right connector respectively disposed on a left side and a right side of the lifter; and a central connector attachable to or detachable from the left connector and the right connector, wherein the left connector comprises:

a first connecting member connected to an upper end of the lifter on the left side of the lifter; and a second connecting member connected to a lower end of the lifter on the left side of the lifter, and the right connector comprises:

another first connecting member connected to an upper end of the lifter on the right side of the lifter, and another second connecting member connected to a lower end of the lifter on the right side of the lifter, wherein the central connector comprises:

a first central connecting member to be connected to the first connecting member and the another first connecting member; and a second central connecting member to be connected to the second connecting member and the another second connecting member, wherein the central connector comprises an indicator configured to indicate a connection location of the left connector or the right connector based on a body size of a user, wherein the left connector or the right connector comprises an edging member extended from an upper end and a lower end of the lifter to cover an outer side of the left connector or the right connector, and a sum of a distance from an end of the central connector to the indicator and a width of the edging member is less than or equal to ½ of a total length of the central connector.

* * * * *